PEAR TREE
Filed March 5, 1975
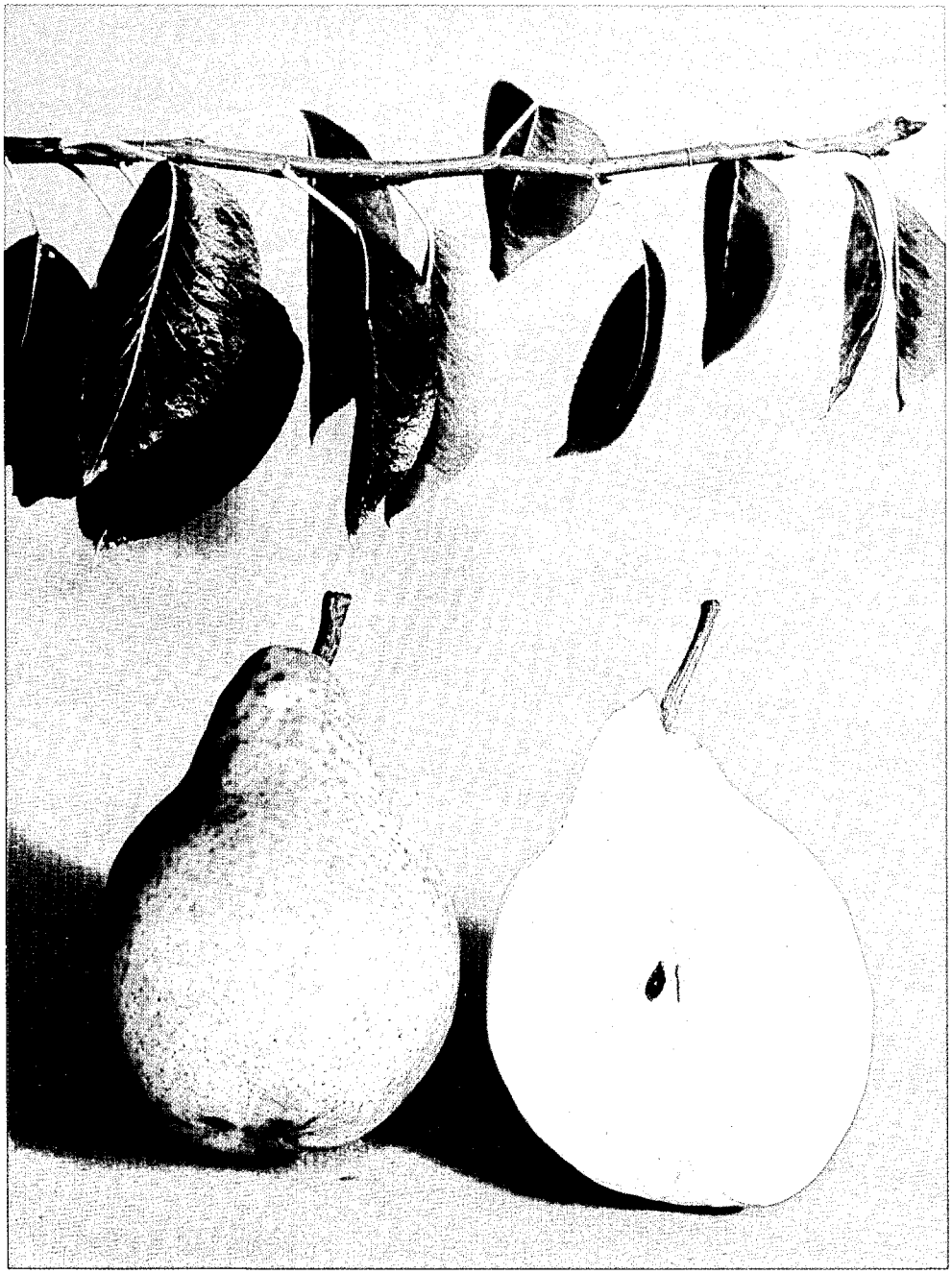

United States Patent

Plant Pat. 3,928

Patented June 29, 1976

3,928

PEAR TREE

Louis F. Johnson, deceased, late of Ukiah, Calif., by Margaret M. Johnson, administratrix, Ukiah, Calif., assignor to Stark Brothers Nurseries & Orchards Company, Louisiana, Mo.

Filed Mar. 5, 1975, Ser. No. 555,449

Int. Cl.[2] A01H *5/03*

U.S. Cl. Plt.—36 1 Claim

ABSTRACT OF THE DISCLOSURE

A pear tree originated as a limb mutation of a Bartlett pear.

SUMMARY OF THE INVENTION

This invention relates to improvements in pear trees of the Bartlett type.

It was originated in Mendocino County, Calif., as a limb mutation of a Bartlett pear.

It is similar in type to the Bartlett pear, although the fruit is much larger, while the tree is appreciably smaller, being semi-dwarf. It has been asexually reproduced by budding.

DETAILED DESCRIPTION OF DRAWING

The accompanying drawing shows typical specimens of the foliage and fruit (in side view and in section) of the new variety as depicted in color as nearly true as is reasonably possible to make the same in a color illustration of this character.

DETAILED DESCRIPTION OF DISCLOSURE

The following is a detailed description of my new variety with color terminology in accordance with Ridgway's Color Standards and Nomenclature, as indicated, except where general color terms of ordinary dictionary significance are obvious.

The specimens described were grown in Mendocino County, Calif.

The first and last picking was from August 15 to August 20.

Tree: Medium small; medium vigor; spreading; low height (average from 14–16 feet); vase formed; slow growing; hardy; medium productive; regular bearing.

Trunk: Stocky; shaggy.

Branches: Medium slender; medium smooth; little branching; green.

Lenticels: Medium few; small.

Leaves: Length, 2½ inches; width, 1⅞ inches; medium small; wide; medium short; oval; abruptly pointed; medium thick; dark green; smooth.

Margin: Finely serrate.

Petiole: Length, ½ inch; medium short; medium thick.

Flowers: Dates of first and full bloom: April 10 and April 17; medium size; white.

Fruit: Maturity when described, eating, ripe, Aug. 12, 1974.

*Size.*—Rather uniform; axial diameter 4¼ inches; transverse 3¼ to 3¾ inches; oblong, obtuse pyroform.

*Cavity.*—Unsymmetrical; very small lipped; depth 1/16 inch; breadth ¼ inch; markings russet—Old Gold Plate XVI Color m 19′ tone i—Ridgway.

*Basin.*—Symmetrical; flaring wide; undulate; glabrous; depth 5/16 inch; breadth 1¼ inches; markings none.

Stem: Clubbed; stout; pubescent; length 1⅛ inches; breadth ¼ inch.

Calyx: Open; based segments persistent; tips deciduous; narrowly lanceolate; length ¼ inch; separated; prostrate; converged from base toward center; outer surface pubescent; inner surface pubescent.

Eye: Large; open.

Skin: Thick; tough; glossy; oily.

*Dots.*—Conspicuous; many; small; even; circular.

*Color of dots.*—Old Gold Plate XVI Color No. 19′ tone i—Ridgway.

*Ground color.*—Yellow Green Plate VI color No. 31 tone—Ridgway.

*Bloom.*—Wanting.

*Scarfskin.*—Wanting.

*General color effect.*—Yellow Green Plate VI Color No. 31 tone—Ridgway.

Flesh: Juicy.

*Color of flesh.*—Satiny; white; greenish tint.

*Texture.*—Soft; fine; melting.

*Flavor.*—Sweet; sprightly.

*Aroma.*—Distinct.

*Quality.*—Good.

Core: Distant.

*Bundle area (longitudinal section).*—Small; orbicular; symmetrical.

*Halves of area.*—Equal.

*Bundles green tinge.*—Inconspicuous in one whorl.

*Alternate bundle.*—Above stamens.

*Core lines.*—Clasping in cross section; carpellary area indistinct; small.

*Calyx tube.*—Glabrous; funnel form.

*Stem of funnel.*—Long.

*Depth of tube.*—To shoulder ⅜ inch; entire depth 17/32 inch; styles present; fleshy; distinct; glabrous throughout.

*Stamens.*—One whorl; marginal.

*Axillary cavity.*—Present.

*Seed cells axile.*—Closed.

*Cell walls.*—Approximate; thin; tough; length 9/16 inch; breadth 5/16 inch.

*Longitudinal section.*—Obovate; obtuse at apex.

*Surface.*—Entire smooth.

*Cross section.*—Narrow.

Seeds:

*Number.*—Perfect: 0 to 5; imperfect: 0 to 3.

*Number in one cell.*—1; length 7/16 inch.

*Breadth.*—3/16 inch.

*Form.*—Acuminate.

*Color.*—Brown—Cinnamon Brown Plate XV Color No. 15′ tone k—Ridgway.

Keeping quality: Medium.

*Number of days in ordinary storage.*—15.

The limb mutation of the Bartlett pear herein described is similar to the Bartlett pear in flavor, texture, skin characteristics, and time of ripening, but the fruit averages 4¼ inches in axial diameter and 3¼ to 3¾ inches in transverse diameter, as compared with the Bartlett which averages 3⅜ inches in axial diameter and 2⅜ inches in transverse diameter; the fruit is not as pyriform in shape as the Bartlett, being more roundish but with a distinct neck. The tree is more compact average height of 14–16 feet, as compared to the Bartlett tree which averages 16–18 feet, being semi-dwarf in size at maturity.

What is claimed is:

1. A new and distinct variety of pear tree substantially as herein shown and described, characterized particularly as to novelty by its fruit being appreciably larger in size than the Bartlett, not as pyriform in shape and more roundish with a distinct neck, while the tree is more compact than the Bartlett tree.

No references cited.

ROBERT E. BAGWILL, Primary Examiner